United States Patent [19]
Porte et al.

[11] Patent Number: 5,424,837
[45] Date of Patent: Jun. 13, 1995

[54] TUBE DIAMETER MEASURING APPARATUS AND METHOD

[76] Inventors: Johannes J. Porte; William D. Van Arsdale; Christopher E. Thomas; James D. Riall; Thomas A. Wertman, all of Eastman Kodak Company, Rochester, N.Y. 14650

[21] Appl. No.: 111,810

[22] Filed: Aug. 25, 1993

Related U.S. Application Data

[63] Continuation-in-part of Ser. No. 948,406, Sep. 21, 1992, abandoned.

[51] Int. Cl.6 ............................................. G01B 11/02
[52] U.S. Cl. ...................................... 356/384; 33/522; 33/555.1; 33/783
[58] Field of Search ................... 356/384–387, 356/244, 246; 250/500, 561; 33/549, 555.1, 555.2, 555.3, 555.4, DIG. 21, DIG. 3, 522, 783, 784, 791, 805; 422/58, 65, 73, 102

[56] References Cited

U.S. PATENT DOCUMENTS

| | | | |
|---|---|---|---|
| 3,568,372 | 3/1971 | Asano et al. | 33/555.1 |
| 3,680,967 | 8/1972 | Engelhardt | 356/246 |
| 3,846,916 | 11/1974 | Moriya et al. | 33/555.1 |
| 3,962,792 | 6/1976 | Stepanek et al. | 33/555.1 |
| 4,122,608 | 10/1978 | Hopf | 33/549 |
| 4,136,455 | 1/1979 | Owsen | 33/555.1 |
| 4,606,130 | 8/1986 | Vetter | 33/555.1 |
| 4,921,676 | 5/1990 | Otani | 422/100 |
| 5,054,205 | 10/1991 | Danielli | 33/555.1 |
| 5,070,623 | 12/1991 | Barnes | 33/555.3 |
| 5,099,585 | 3/1992 | Liskow | 33/555.1 |
| 5,154,003 | 10/1992 | Moore | 33/555.1 |

FOREIGN PATENT DOCUMENTS

471980 2/1992 European Pat. Off. .

Primary Examiner—Hoa Q. Pham
Attorney, Agent, or Firm—Dana M. Schmidt

[57] ABSTRACT

A container of sample tubes is described with a mechanism for detecting the diameter of variously sized tubes that are placed therein. A method of detection is also described. Both the mechanism and the method rely on pairs of tube holders that are biased together with detectable ends that are spaced farther apart, the larger the tube that is held by the holders. A sensor is provided externally of the container to sense how far apart the ends are spaced.

16 Claims, 7 Drawing Sheets

TUBE DIAMETER MEASURING APPARATUS AND METHOD

RELATED APPLICATIONS

This application is a continuation-in-part application of U.S. Ser. No. 07/948,406, filed Sep. 21, 1992, now abandoned.

FIELD OF THE INVENTION

This invention relates to containers of sample tubes useful in an analyzer, and specifically to a mechanism and method for detecting the diameter of tubes present, which can vary.

BACKGROUND OF THE INVENTION

It is known to mount sample tubes in a tube holder in an analyzer, the holder having a well for each tube. Examples are shown in U.S. Pat. No. 3,680,967 and in EPA 471980 (Docket 60,752). In the former, pairs of spring fingers in each well are used to grip a tube, but no attempt is made to determine the tube diameter, since apparently only one diameter is contemplated. In the latter, varying tube diameters are in fact sensed, in an effective and accurate manner. However, the sensor requires a large, spring biased probe, FIG. 3, which has the disadvantage of excessive size. Still further, the sensor pushes the tube to the inside of the holder as part of the sensing process. Although the sensor determines that in fact the tube center has become displaced from the center of the well, this still requires the analyzer to make an adjustment in the vertical plane, before descending to sample the tube, to avoid the aspirator contacting the tube sidewall.

Therefore, prior to this invention there has been a need to provide a tube-sensing apparatus that is less expensive and less substantial than those required heretofore, which automatically centers the tube with the center of the well, no matter what the tube size is.

RELATED APPLICATIONS

A tube container comprising a tray similar to that described herein is disclosed in commonly owned U.S. application Ser. No. 859,780 filed on Mar. 30, 1992 by D. A. Tomasso et al, entitled "Tray and Magnetic Conveyor". However, the tray or container therein lacked the diameter measuring apparatus featuring the sensing means of the instant invention.

SUMMARY OF THE INVENTION

We have constructed a tube diameter measuring apparatus that meets the above-noted need of reduced costs.

More specifically, there is provided in accordance with one aspect of the invention, a tube diameter measuring apparatus for use in a sample tube container having a well for each tube, the apparatus comprising
 a signaller for at least some of the tube wells and comprising
 a reference finger on the apparatus at a home position,
 and in at least some wells, a movable finger pivotally mounted on the apparatus to move into or out of each of the at-least-some wells, and a spring biasing each movable finger to move into its respective well, and sensing means exterior of the apparatus for sensing the distance the ends of a pair of fingers in a given well are spaced apart, and for generating a signal that converts that distance into a tube diameter.

In accord with another aspect of the invention, there is provided a method of automatically determining the size of a tube inserted into a tube container having a well for each tube and a pair of fingers for at least one well,
 the method comprising the steps of a) inserting a tube of one of at least two alternative diameters into a well so as to spread apart at least one of the ends of the fingers a distance controlled by the diameter of the tube, and b) measuring the distance apart of the finger ends as a function of the tube diameter.

Accordingly, it is an advantageous feature of the invention that the tube container, also called a tray in other publications, itself includes signalling means by which the diameters of the contained tubes can be automatically sensed.

It is a related advantageous feature of the invention that such a container uses signalling means that also help retain tubes from rotating within the container.

Yet another related advantageous feature is that the signalling means in at least one embodiment, automatically centers the tube with the center of the well, no matter what the tube size.

It is another related advantageous feature that such signalling means are inexpensively provided due to their simplicity.

Other advantageous features will become apparent upon reference to the following Detailed Description when read in light of the attached drawings.

DESCRIPTION OF THE PREFERRED EMBODIMENTS

The invention is described hereinafter by references to the preferred embodiments, in which a generally cylindrical tube container is used with patient sample tubes and disposable aspirating tips in a clinical analyzer for doing wet assays, the container having means for providing sensing of tube diameters and, conveying means for the container(s) that moves trays in a closed loop. In addition, the invention is useful regardless of the overall shape of the container(s) or its particular incorporation in an analyzer, and regardless of whether or not the sensing means are also used to prevent sample tubes from rotating, or what type of sensing means are used. That is, it is useful regardless of what part of the electromagnetic spectrum is used in the sensing means.

The invention features a signaller associated with at least some tube wells of a tube container. As used herein, a signaller comprises a mechanism for initiating a signal representing tube size, based upon the position of relevant parts of the signaller. As will be seen, in some embodiments it comprises a pair of fingers or tube holders. The signaller in turn cooperates with a sensing means.

Figure 1:
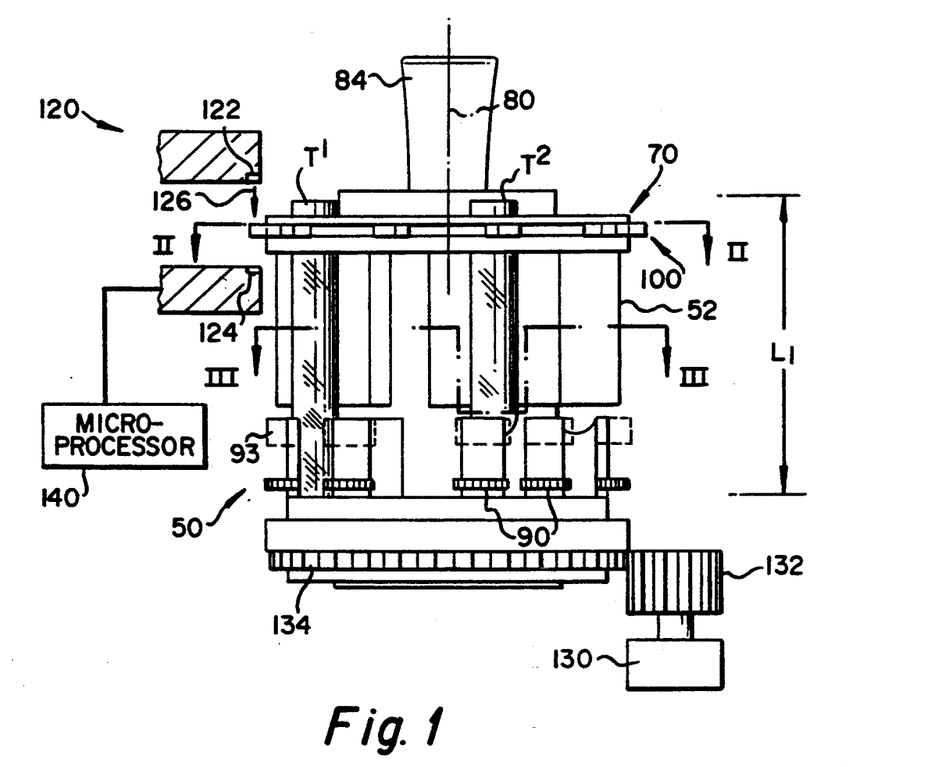
FIG. 1 is a fragmentary side elevational view of a tube container constructed in accordance with the invention.

Thus, the preferred construction, FIG. 1, is one in which tube containers 50 are provided for supplying sample-containing tubes to a clinical analyzer, and specifically to an aspirating station of the analyzer. (The details of the aspirator are not included, as they can be conventional and do not comprise the invention. However, they preferably include a conveyor, described hereinafter.)

The containers 50 are preferably removably and rotatably mounted on bases 30 (FIG. 4), and specifically preferably to rotate concentrically about spindles 38, as described and claimed in the aforesaid U.S. Ser. No. 859,780, FIG. 4. Such a container comprises a frame 52 having a bottom portion 54 recessed at 56 and 58 to receive housing 34 and spindle 38, respectively.

Figure 2:
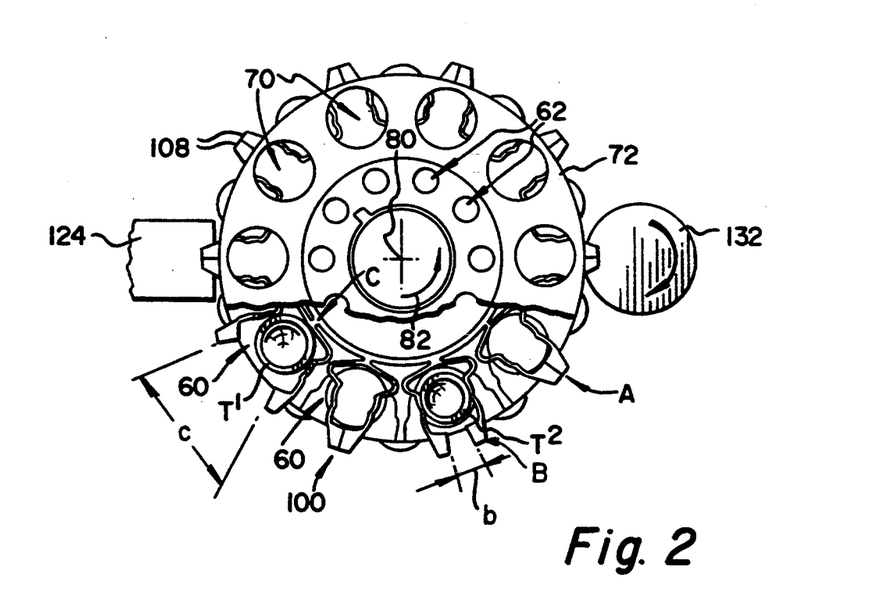
FIG. 2 is a fragmentary plan view partially broken away along the line II—II of FIG. 1.

Frame 52 further comprises a plurality of receptacles 60 and 62, FIG. 2, to receive conventional sample tubes T and conventional aspirating tips, respectively, where tubes T can be of varying sizes $T^1$ and $T^2$. Receptacles 60 preferably comprise bottom portion 54 providing a fixed bottom support having therein fixed sockets 66, FIG. 4, forming cylindrical recesses, and directly vertically above the sockets, means 70 defining circular apertures. Preferably, a ring 72 extends out over sockets 66, FIG. 4, to provide an upper support for tubes T, since it is in this ring 72 that apertures 70 are formed, most preferably so as to be vertically aligned with sockets 66. The internal diameters of sockets 66 and apertures 70 are such as to accommodate the largest tubes $T^1$ of sample that are to be used.

Figure 3:
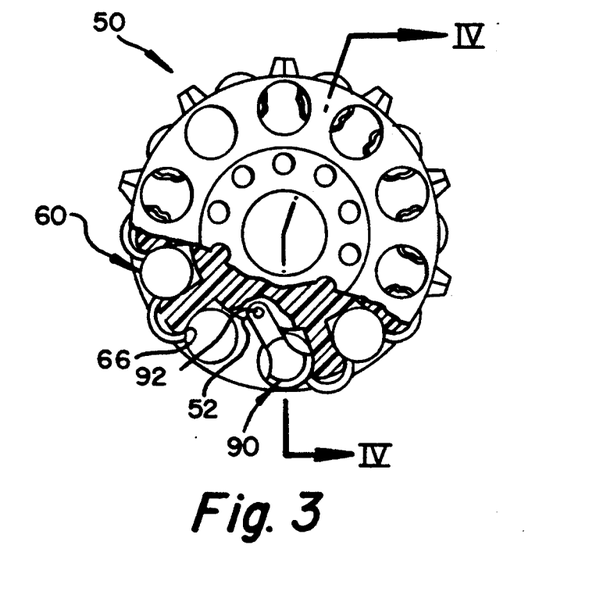
FIG. 3 is a section view taken generally along the line III—III of FIG. 1, the sensor and drive means of FIG. 1 having been omitted for clarity.

Apertures 70 are shown, FIGS. 2 and 3, as formed by a complete closure in ring 72. Optionally, however, a small gap in the closure is tolerable, provided it is not large enough to allow a tube to fall out.

Figure 4:
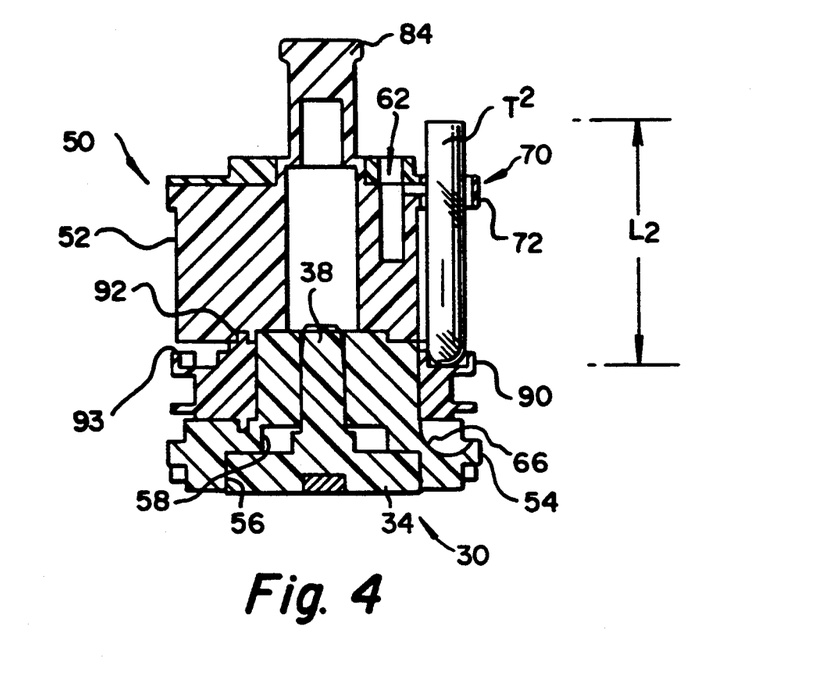
FIG. 4 is a section view taken generally along the line IV—IV of FIG. 3.
Figure 6:
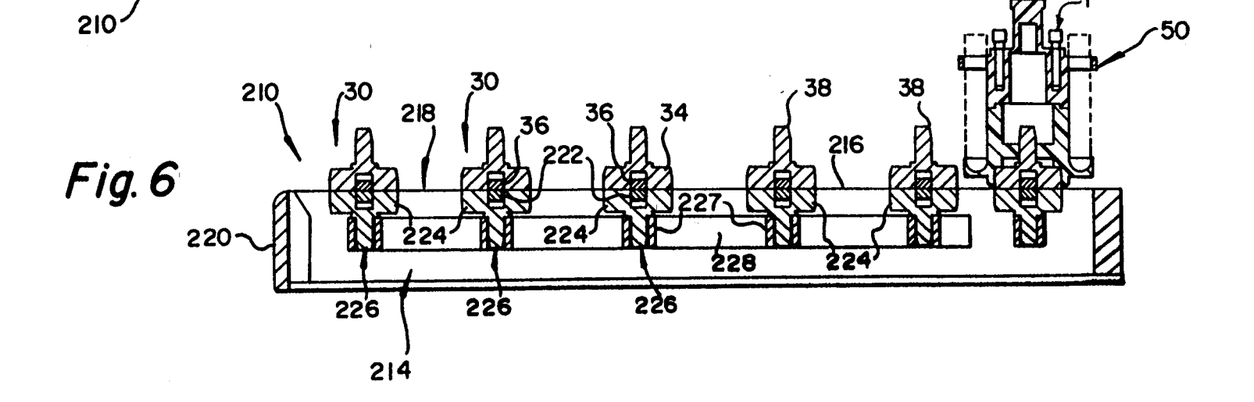
FIG. 6 is a section view taken generally along the line VI—VI of FIG. 5, the tube container having been simplified for illustration.

Receptacles 62, FIG. 4, can be simple cylindrical bores extending preferably vertically down into frame 52, of a size and shape to hold dispensing tips t (shown in FIG. 6) therein by their fins. Receptacles 62 thus preferably form a concentric ring, FIGS. 2 and 3, that is preferably inside the concentric ring formed by receptacles 60, although the ring of receptacles 62 can also be outside the ring of receptacles 60 if ring 72 is extended considerably farther from axis 80, FIG. 1, the axis of symmetry of tray 50.

Axis 80 is also preferably the axis of rotation, arrow 82, of tray 50, FIG. 2. Such rotation can be achieved manually, for example, by using handle 84 that is mounted preferably on axis 80, FIG. 1. Preferably, it is rotated mechanically by means hereinafter described.

Tips t need not have more than one size. However, tubes T conventionally come also in at least 2 sizes. For example, tube $T^2$ comes with length $L_2$, FIG. 4, with or without the same diameter for tube $T^1$, having length $L_1$. Accordingly, containers 50 can include a second, movable bottom support 90, FIGS. 1 and 4, for such shorter tubes, and means 92 for pivotally and permanently mounting supports 90, FIG. 4, on frame 52 between the fixed bottom support of portion 54 and the upper support of ring 70. Support 90 includes a vertically extending shoulder 93, which can be a partial ring (as shown), or a complete ring to provide a socket for supporting tube $T^2$. Such an arrangement permits movable supports 90 to pivot into or out of alignment with apertures 70 (and the bottom support of sockets 66), to allow either a tube $T^2$ of length L2 or tube $T^1$ of length L1, respectively, to be supported. At the same time, support 90 remains attached at all times to frame 52, even when not in active use. As shown in FIG. 4, pivot means 92 comprise pins that permit pivoting of movable supports 90 about a vertical axis.

Alternatively, not shown but described in the aforesaid U.S. Ser. No. 859,780, the pivoting bottom supports 90 can be mounted to pivot about a horizontal, rather than vertical, axis.

In accordance with the invention, containers 50 are provided with a tube measuring apparatus, that preferably comprises a signaller integrally mounted in the container, and signal-sensing means exterior of the container.

More specifically, the signaller comprises a pair of complementary tube holders 100, FIG. 1, for each well 60, mounted in ring 70, the holders being generally shaped like gripping fingers. One of these fingers can be considered a reference finger. Each finger of each pair comprises a base portion 102, FIG. 8, a pivot site portion 104, a tube-contacting portion 106, and a flag portion 108 located preferably at the end of each finger. Most preferably, each pair of tube holders 100 is connected to all the other pairs in a continuous ring. Alternatively, each pair can be separate from the others and attached to frame 52 within ring 70. Importantly, tube holders 100 are manufactured from elastic, springy material so that ends 108 are biased together in the absence of a tube. For example, spring steel such as stainless steel "310" or "410" can be used.

As will be clearly seen from FIG. 2, ends 108 project outwardly from ring 72 a distance sufficient to be sensed by sensor 120 described below.

Figures 7, 8:
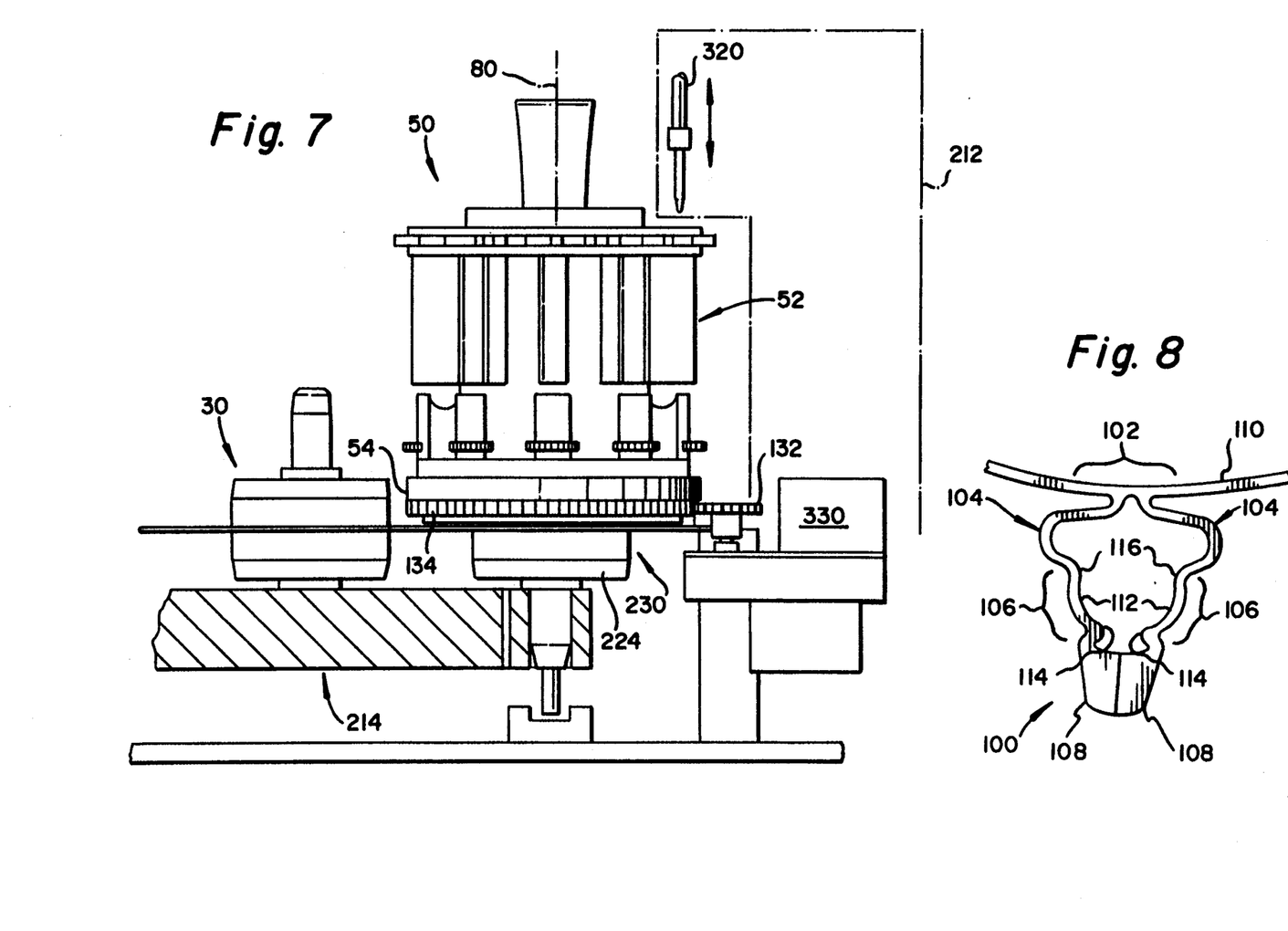
FIG. 7 is a fragmentary section view taken generally along the line VII—VII of FIG. 5.
FIG. 8 is a fragmentary plan view (enlarged of a pair of tube holders shown in FIG. 2.

Tube-contacting portion 106, FIG. 8, can have any configuration. Most preferably, however, it is shaped so as to help grip a contained tube and prevent it from rotating, as shown in FIG. 2 for tube $T^2$. To that end, portion 106 preferably comprises a concave surface 112 bordered by convex surfaces or bumps 114 and 116. Most preferably, opposing portions 106 do not contact in the absence of a tube, to ensure that ends 108 do contact.

It will be readily appreciated, FIG. 2, that ends 108 are caused to be spaced apart a variable distance that depends upon the diameter of a tube inserted between the fingers of a tube holder 100. Thus, at position "A", no tube is present and ends 108 have no spacing between them. At position "B", a smaller tube is present, providing spacing "b". At position "C" a larger tube is present, providing spacing "c". It is these spacings of zero, "b", or "c" that are to be sensed. The smaller and larger tube sizes are selected to correspond with the conventional tube sizes most commonly used in the analyzer field, e.g., sizes of 13 and 16 mm, respectively.

The external sensor 120, FIG. 1, can comprise any means for sensing the distance the ends 108 are spaced apart. Most preferably, it comprises a conventional electromagnetic radiation emitter 122 and receiver 124, for example, an infrared emitter producing a beam 126 detected by an infrared detector. Also, most preferably, beam 126 is aligned so as to be generally parallel to the axis of tube $T^1$ or $T^2$. As used herein, "generally parallel" includes misalignment out of parallel as much as 5°. However, most preferably any misalignment of beam 126 still confines the beam within a plane defined by the axis of tube $T^1$ or $T^2$, and axis 80, since that is least likely to interfere with the accurate detection of ends 108 of tube holders 100.

To move ends 108 of the tube holders through beam 126, moving means are provided, such as a drive motor 130. Most preferably, motor 130 drives a drive pinion gear 132 that engages a rack gear 134 on frame 52, to cause frame 52 to rotate about axis 80, and hence each pair of tube holders to pass through beam 126. A microprocessor 140 is also part of the external sensor, to receive signals from receiver 124. That is, first a first beam interrupt is detected to start the "count". This interruption occurs when the first end or flag 108 of a pair passes through beam 126. When the beam resumes, a measurement is made of the rotated distance that occurs before the next interrupt caused by the other end or flag 108. A suitable measurement would be, for example, the number of steps generated by motor 130 if that motor is a stepper motor. Those steps are then calculated by the microprocessor. Alternatively, the microprocessor can compare the number of steps with a look-up table that has a predetermined range of steps for each diameter tube $T^1$ or $T^2$, that is, corresponding to spacing "b" or "c".

Sensor 120 determines no tube is present when no resumption of beam 126 occurs after the number of steps occurs that will pass a single flag or end 108 through the beam.

Environment of Use

As noted, especially in U.S. Ser. No. 859,780, containers 50 are preferably used in a sample station 200 of an analyzer, FIG. 5. Such a station includes a conveyor 210. Conveyor 210 in turn includes bases 30 on which containers 50 are removably mounted, and means 214, FIG. 6, for conveying bases 30 and containers thereon around on the top surface 216 of an impermeable support 218, held in placed by frame 220 of the analyzer. Most preferably, conveying means 214 comprise a plurality of magnets 222, at least one of the magnets each being held in a housing 224 journalled at 226 in an aperture of a projecting lug 227, FIG. 5, of a continuous belt 228 driven by a suitable pulley 229 and a conventional motor, not shown. Thus, there is provided a housing 224, FIG. 6, and at least one magnet 222 to correspond to each base 30. Each housing 224 and base 30 is then caused to circulate around the path 231, FIG. 5, as directed by belt 228. The advantage of such a conveying means is, of course, that liquids spilled, if any, out of the tubes will not contact the conveying mechanisms comprising housings 224 and belt 228.

Figure 5:
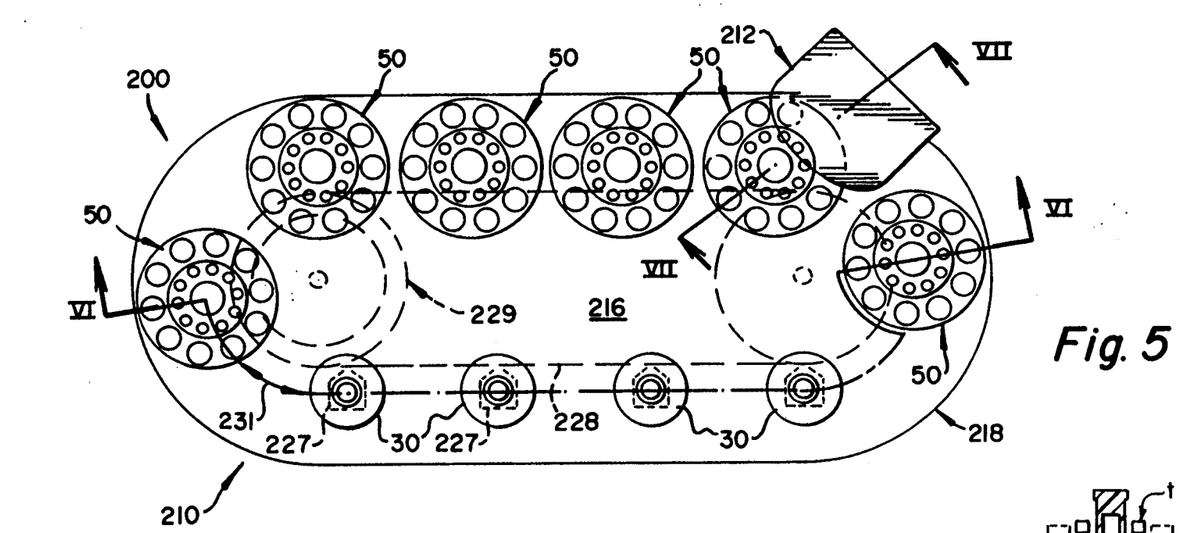
FIG. 5 is a plan view of a supply station in an analyzer useful with the tube containers of the invention.

Conveyor 210 moves containers 50 into position at aspirator station 212, FIG. 5, which includes a conventional aspirator 320, FIG. 7. However, because of the free rotation of containers 50 on base 30 about axis 80, it is preferred that each container be positively rotated to place the desired sample tube directly under aspirator 320. This is achieved by gear 132 driving rack 134 on the circumference of bottom portion 54, as described above. Conveying means 214 is effective to force gear 132 into engagement with gear 134. The magnetic coupling of each container to conveying housings 224 is sufficiently compliant to accommodate any inadvertent misalignment of gear teeth at the time of meshing. A signalling means in turn is used to designate at least a "home" position, and to this end any flag (not shown), e.g., a projecting shoulder, a magnet, or a light reflector is disposed on frame 52, e.g., adjacent bottom portion 54, for detection by detector 330.

Sensor 120 can be conveniently mounted on aspirator station 212.

Aspirator 320 then is used to dispense sample into a reaction cuvette or onto a dried test element, not shown, for testing using any convenient apparatus (not shown). For example, the apparatus taught in commonly-owned U.S. Ser. No. 887,990 filed on May 22, 1992 by Jakubowicz et al entitled "Analyzer Incubator with Plural Independently Driven Rings Supporting Cuvettes" is useful.

Alternative Embodiments

Figure 9:
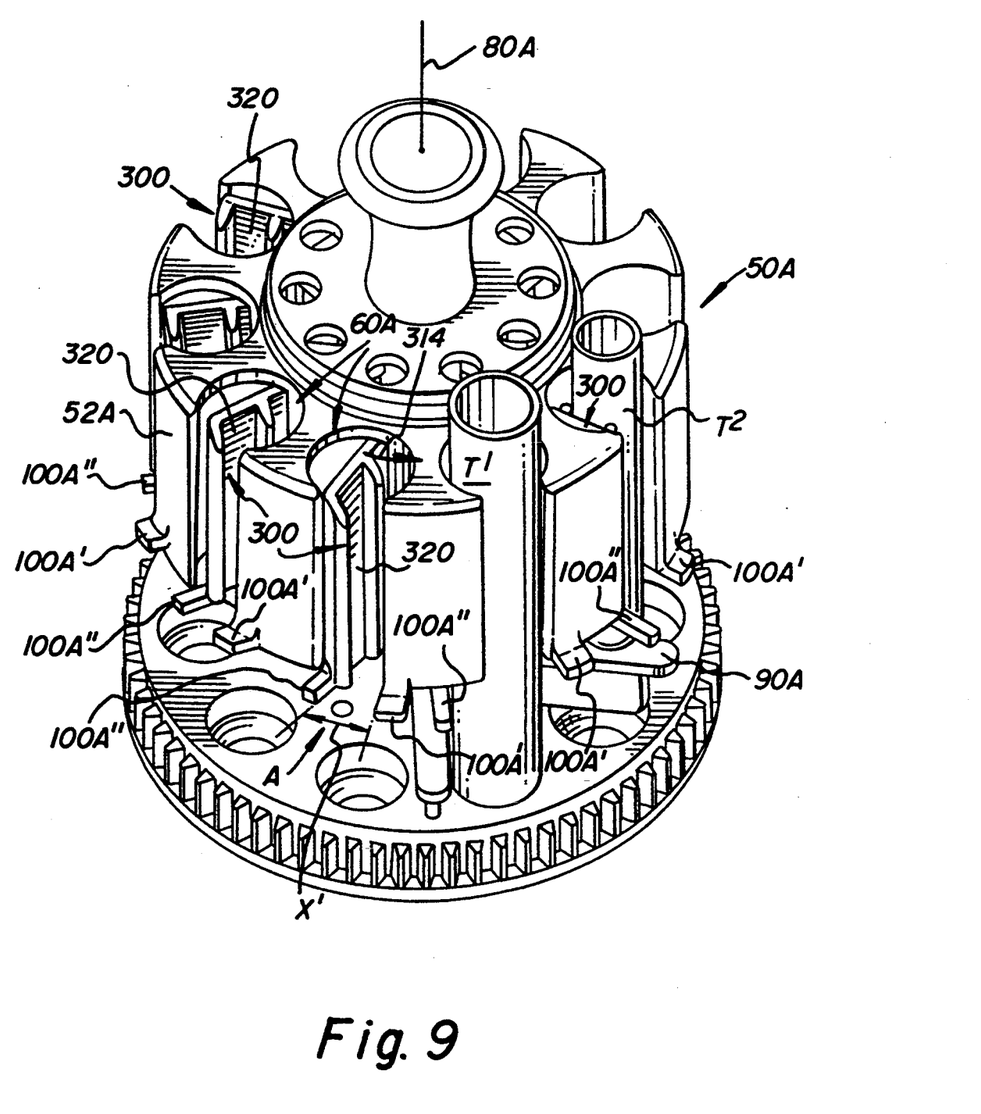
FIG. 9 is an isometric view of a tray using the sensing apparatus of the invention, showing an alternative embodiment.
Figure 10:
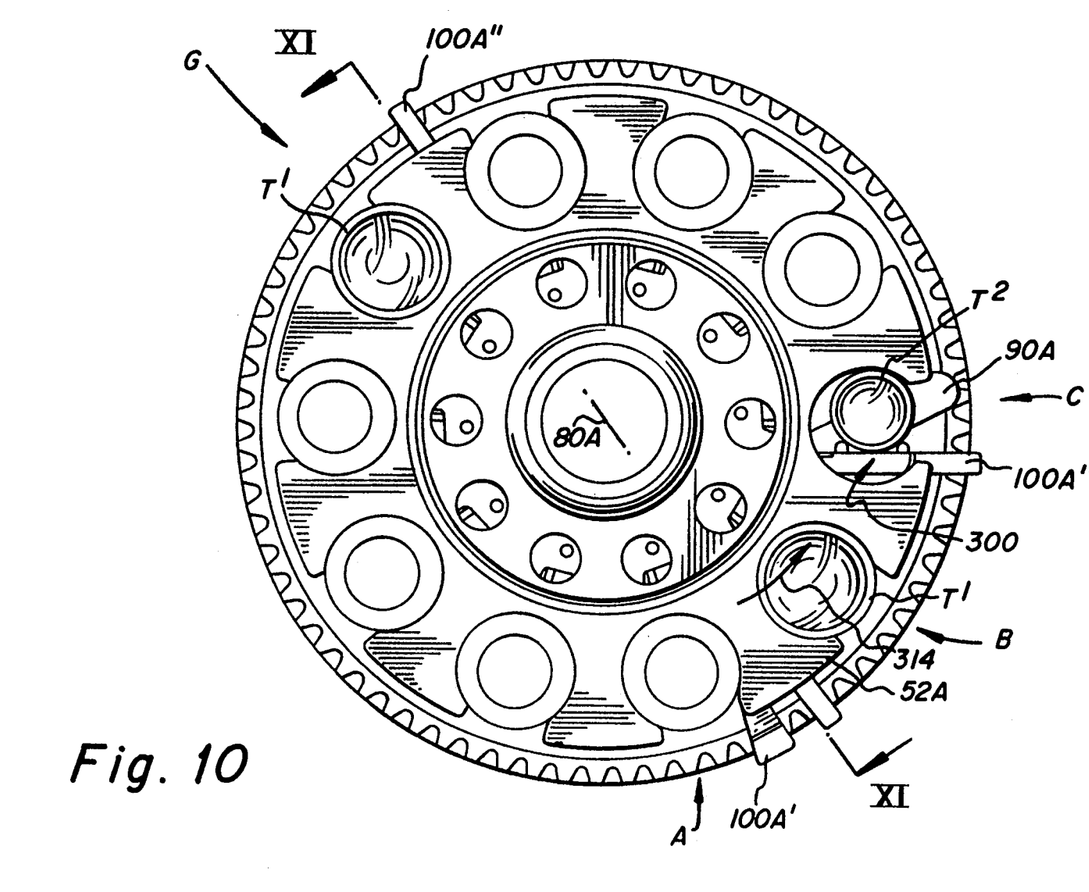
FIG. 10 is a plan view of both the embodiment of FIG. 9 and an alternate embodiment.
Figure 11:
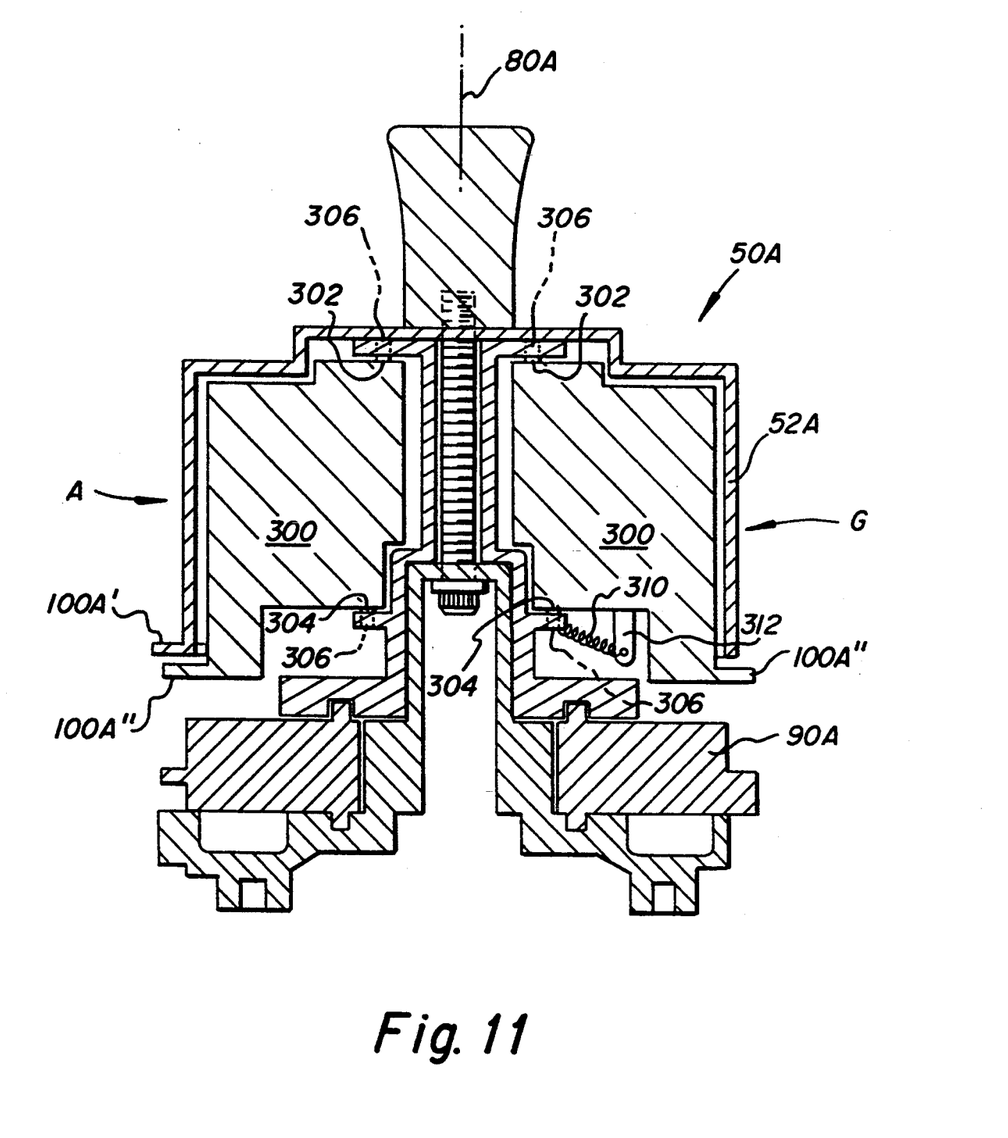
FIG. 11 is a section view taken generally along the line XI—XI of FIG. 10.

It is not necessary that both fingers of the pair be pivotable or movable, only that one be. Still further, there need be only one reference finger for the entire circumference. Both of these alternatives are shown in FIGS. 9-11, wherein parts similar to those previously described bear the same reference numerals, to which the distinguishing suffix A is appended. (The analyzer or "environment" in which these embodiments are used remain the same as heretofore, and hence are not further described.)

Thus, FIG. 9, the signaller comprises a pair of fingers at each well 60A in a tray 50A, and having detectable ends, the tray being constructed generally as heretofore described, including pivotable alternative supports 90A. The exception is that one of each pair of fingers, 100A', is fixed to the outside of frame 52A, such as at one of said wells as shown, and only the other of the pair, finger 100A", is movably mounted, preferably by pivoting a paddle 300 from which finger 100A" extends. That is, paddles 300 have a pivot 302 and 304 at the upper and lower edges, FIG. 11, which are journalled in frame 52A at 306. To bias each finger 100A" into its well, and hence operationally towards the reference finger 100A", an extension spring 310 is used to connect a portion 312 of each paddle to frame 52A at the opposite side (not labeled) of each well. The biasing action is in the direction of arrow 314, FIGS. 9 and 10, so that finger 100A" closes towards (but not in contact with) finger 100A', in the absence of a tube in that well. (For purposes of this embodiment, shown in FIG. 9, additional fixed fingers 100A' and 100A" would of course be present in FIG. 10, but for simplicity, they are not shown.) A stop surface (not shown) is effective to prevent finger 100A" at station A, FIG. 9, from closing closer to finger 100A' than is shown.

Optionally, a rounded surface 320 can be vertically applied to paddles 300 to fit snugly against a tube in the well.

Because fingers 100A' and 100A" are no longer near the top of frame 52A, the external sensor (not shown) corresponding to sensor 120 of the previous embodiment, is moved down to the new "level" of the fingers. Otherwise, it operates as described before. That is, the spread between fingers 100A' and 100A" is controlled largely by the diameter of tube $T^1$ or $T^2$, FIGS. 9 and 10, that is present in the well. The sensor can easily detect the difference between $X^1$, FIG. 9, the spreads created by those sizes, and the spread when no tube is present.

Because tray 50A can spin about its vertical axis 80A, as in the previous embodiment, it is not even necessary that there be more than one fixed finger 100A' present, as actually shown in FIG. 10. That is, the sensor (such as sensor 120 of FIG. 1) will detect the number of half-step rotations that each of the movable fingers 100A" are located from single finger 100A', designated the home position, which of course is a known function of the spread, if any, of the paddle of each well being created by a tube present, if any. (Since only the wells at station B, C and G, FIG. 10, have tubes therein, fingers 100A" are shown only for those wells.)

The invention disclosed herein may be practiced in the absence of any element which is not specifically disclosed herein.

The invention has been described in detail with particular reference to preferred embodiments thereof, but it will be understood that variations and modifications can be effected within the spirit and scope of the invention.

What is claimed is:

1. A sample tube container and tube diameter measuring apparatus, said sample tube container having a well for each tube, the container and apparatus comprising:
   a signaller for at least some of the tube wells, which signaller comprises
   a reference finger on said container at a home position,
   and in said at least some wells, a movable finger pivotally mounted on the container to move into and out of each of said at least some wells, each of said fingers having an exposed end, and a spring for biasing each movable finger to move into its respective well, and sensing means exterior of said container for sensing at what distance, if any, said end of a movable finger in a given well is spaced apart from said reference finger, and for generating a signal that converts said distance into a tube diameter.

2. A tube container and tube diameter measuring apparatus as defined in claim 1, wherein said reference finger is fixed to said container at least one of said wells.

3. A tube container and tube diameter measuring apparatus as defined in claim 2, wherein said reference finger comprises the only fixed finger on said apparatus.

4. A tube container and tube diameter measuring apparatus for use in a sample tube container having a well for each tube, the apparatus comprising:
   a signaller mounted in at least some of the tube wells and comprising a pair of complementary fingers, each finger of said pair extending from a pivot point to an end of the finger, and each finger including a tube-contacting portion between said pivot point and said finger end, said fingers being bent about said pivot point so as to be biased towards each other and to contact each other at said ends in the absence of a tube,
   and sensing means exterior of said apparatus for sensing the distance said ends of a pair of fingers in a given well are spaced apart, and for generating a signal that converts said distance into a tube diameter.

5. A tube container and tube diameter measuring apparatus as defined in claim 4, wherein said tube-contacting portion includes means for preventing a tube from rotating in a well when contacted by said fingers.

6. A tube container and tube diameter measuring apparatus as defined in claim 5, wherein said contacting portion comprises a concave surface bordered by two convex surfaces.

7. A tube container and tube diameter measuring apparatus as defined in claims 4 or 5, wherein said contacting portions are spaced apart from each other in the absence of a tube in the well in which said fingers are disposed.

8. A tube container and tube diameter measuring apparatus as defined in claim 4, wherein said sensing means senses from the spacing-apart of said finger ends, whether there is not tube present, a small tube present, or a large tube present.

9. A tube container and tube diameter measuring apparatus as defined in claims 4 or 8, wherein said sensing means comprise an electromagnetic radiation emitter and receiver separate from said container, said emitter and receiver being disposed so that the radiation is emitted in a beam that generally parallels the axis of a tube in a well between said pair of fingers,
   means for moving said pair of fingers past said emitter so that said ends sequentially interrupt said beam, and
   means for ascertaining the distance moved between sequential interrupts of said beam by said ends, and for comparing the ascertained distance against a standard representing a tube diameter.

10. A sample tube container and tube diameter measuring apparatus, said sample tube container having a well for each tube, the container and apparatus comprising:
    a signaller mounted in at least some of the tube wells and comprising a pair of complementary tube holders, each tube holder comprising a base portion, a pivot site portion, a tube contacting portion, and a flag portion, said pivot site portion and said tube contacting portion being located between said flag portion and said base portion, said tube holders being biased together into contact in the absence of a tube,
    a sensor constructed to sense a distance said flag portions of a given pair of tube holders are spaced apart, and
    signal means for generating a signal representing said distance and for converting said signal into a tube diameter.

11. A tube container and tube measuring apparatus as defined in claim 10, wherein said tube-contacting portion includes means for preventing a tube from rotating in a well when contacted by said tube holders.

12. A tube container and tube measuring apparatus as defined in claim 11, wherein said contacting portion comprises a concave surface bordered by two convex surfaces.

13. A tube container and tube measuring apparatus as defined in claim 10 or 11, wherein said contacting portions do not contact each other in the absence of a tube in the well of which said tube holders are disposed.

14. A tube container and tube measuring apparatus as defined in claim 10, wherein said sensor senses from the spacing-apart of said flag portions, whether there is no tube present, a small tube present, or a large tube present.

15. A tube container and tube measuring apparatus as defined in claim 10 or 14, wherein said sensor comprises an electromagnetic radiation emitter and receiver separate from said container, said emitter and receiver being disposed so that the radiation is emitted in a beam that generally parallels the axis of a tube in a well between said pair of tube holders, means for moving said pair of tube holders past said emitter so that said flag portions sequentially interrupt said beam, and wherein said signal means comprise means for ascertaining the distance moved between sequential interrupts of said beam by said flag portions and for comparing the ascertained distance against a standard representing a tube diameter.

16. A method of automatically determining the size of a tube inserted into a tube container having a well for each tube and a pair of fingers for at least one of said wells, the method comprising the steps of a) inserting a tube of one of at least two alternative diameters into a well so as to spread apart at least one of said ends of said fingers a distance controlled by the diameter of the tube, and b) automatically measuring said distance apart of said finger ends as a function of said tube diameter.

* * * * *